United States Patent [19]

Hanny

[11] 4,050,820

[45] Sept. 27, 1977

[54] LIGHT-REFLECTING ANALYTICAL DEVICE

[75] Inventor: John Franklin Hanny, Dayton, Ohio

[73] Assignee: NCR Corporation, Dayton, Ohio

[21] Appl. No.: 658,562

[22] Filed: Feb. 17, 1976

[51] Int. Cl.² .......................................... G01N 21/00
[52] U.S. Cl. ............................ 356/103; 350/160 LC; 356/210; 356/244
[58] Field of Search ............... 356/103, 209, 210, 211, 356/212, 244; 350/160 LC

[56] References Cited

U.S. PATENT DOCUMENTS 3,523,738  8/1970  Chisholm ........................ 356/246 X
3,758,195  9/1973  Hedman, Jr. et al. ........ 350/160 LC

OTHER PUBLICATIONS

Dixon et al., "Thermal Hysteresis in Cholesteric Color Responses", *Molecular Crystals and Liquid Crystals*, vol. 10, No. 3, pp. 317-325, 1970.

Primary Examiner—John K. Corbin
Assistant Examiner—Matthew W. Koren
Attorney, Agent, or Firm—E. Frank McKinney

[57] ABSTRACT

A device is disclosed for spectral analysis of light reflected from liquid crystal materials. The device includes a light source, a liquid crystal material stage, and a scattered light receiving screen. In operation, the liquid crystal material stage and the scattered light receiving screen are submerged in a liquid having an index of refraction greater than about 1.2.

10 Claims, 2 Drawing Figures

LIGHT-REFLECTING ANALYTICAL DEVICE

BACKGROUND OF THE INVENTION

1. Field of the Invention

Cholesteric liquid crystal materials cause incident radiant energy to be spectrally scattered and the spectrum is distinctive to particular environmental conditions. Cholesteric liquid crystal materials exhibit the radiant energy-scattering or light-scattering effect as a function of temperature and as a function of the composition which includes the liquid crystals.

This invention relates to analysis of the light scattering properties of compositions which contain cholesteric liquid crystal materials. It more particularly pertains to a device for causing and observing such light scattering under controlled conditions.

This invention pertains to a device for exposing a light scattering composition to incident light and to a process for exhibiting the scattered light spectrum on a viewing screen. The invention more particularly pertains to such a device wherein the spectrum scattered light is a broad spectral display.

2. Description of the Prior Art

Iridescent reflection of incident white light from cholesteric liquid crystal materials is well known. U.S. Pat. No. 3,114,836 issued Dec. 17, 1963 discloses display devices which utilize cholesteric liquid crystal materials to present thermal patterns or outlines of thermal bodies. The device therein includes a film coated by liquid crystal material and positioned such that an observer normal to the film can watch the liquid crystal material undergo iridescent color change over a period of temperature change in the film.

U.S. Pat. No. 3,441,513 issued Apr. 29, 1969 discloses spectral scattering of white light incident on films of a variety of cholesteric liquid crystal compositions.

Several technical journal articles have discussed temperature sensitive light scattering of liquid crystal materials and devices for observing such light scattering. Examples of pertinent articles are: Fergason, J. L., Molecular Crystals, Volume 1, pp 293–307 (1966); Fergason, J. L., Goldberg, N. N., and Nadalin, R. J., Molecular Crystals, Volume 1, pp 309–323 (1966); and Adams, J., Haas, W., and Wysocki, J., Molecular Crystals and Liquid Crystals, Volume 8, pp 9–18 (1969). The light scattering disclosed therein is not revealed, or understood, to be a spectral reflection from a film at a single temperature.

SUMMARY OF THE INVENTION

Cholesteric liquid crystal materials are combined to provide compositions which exhibit color advent in incident white light at particular temperatures and over specified temperature ranges. The combination of materials is critical to proper performance and the temperature response must be carefully controlled to provide quality assurance to any product using the combination.

The liquid crystal materials themselves are expensive and the value of products which include such materials is correspondingly high. Once combined and introduced into a display product, liquid crystal formulations cannot often be modified or even reclaimed and its result is a loss of the entire value of materials and display.

The testing device of this invention provides a means for determining color advent temperature and temperature response range in liquid crystal formulations. Such determinations are useful for developing new liquid crystal formulations and for quality control purposes of comparison from one batch of a formulation to another.

A small amount of any liquid crystal material to be tested can be mounted in the device of this invention and an entire spectrum of color will be scattered from the material and projected onto the test screen at an appropriate advent temperature and through the temperature response range.

By "light", herein is meant radiant energy including, but not limited to, energy in the visible spectrum.

BRIEF DESCRIPTION OF THE DRAWING

Referring now to FIG. 1, a base 11 of solid structural material has attached, either fixedly or movably thereto, mounting block 12. Mounting block 12 has a smooth mounting surface of, light absorbing, preferably matte, and most often black, finish. Other light absorbing colors can be utilized for special desired or required effects. Arcuate light support 13 is fixed to the base 11 such that the arc is in a plane normal with the mounting surface and the arc radius is centered approximately at the mounting surface. Light source (14) is adjustably fixed to support 13 and can be self-contained or can rely on outside power supply. Projection screen 15 is affixed to screen support 16 which provides a surface normal to the plane of arcuate light support 13. Projection screen 15 is any relatively smooth, light-reflecting, surface and is a light color, preferably and most often white. The projection screen 15 can be self-supported. Liquid crystal material 17 is located on the mounting surface of block 12 in the plane of light support 13 and a transparent protective cover 18 is pressed over the liquid crystal material 17.

Referring now to FIG. 2, which shows the testing device of this invention, as depicted in FIG. 1, in operation. The device is located in vessel 19 and, but for light source 14 and the upper extremity of light support 13, is submerged in fluid 20. The use of fluid 20 is important, as will be seen below, for reasons of light refraction qualities. Incident white light 21 is directed from the light source (not shown) to the film of liquid crystal sample 17 through the protective cover 18. That incident white light 21 is scattered by the film of liquid crystal sample 17 and is reflected up to the projection screen 15 where it is intercepted and exhibited as a spectral display. In a purely exemplary way, solely to indicate the wavelength trend for scattering, it is noted that reflected red light 22 is scattered at a smaller angle to the normal than is reflected yellow-green light 23 and reflected blue light 24. In operation, white light 21 exists between the light source 14 and the film of liquid crystal sample 17 and scattered light of spectral hue 22, 23, 24 exists between the film 17 and the projection screen 15.

Figure 1:
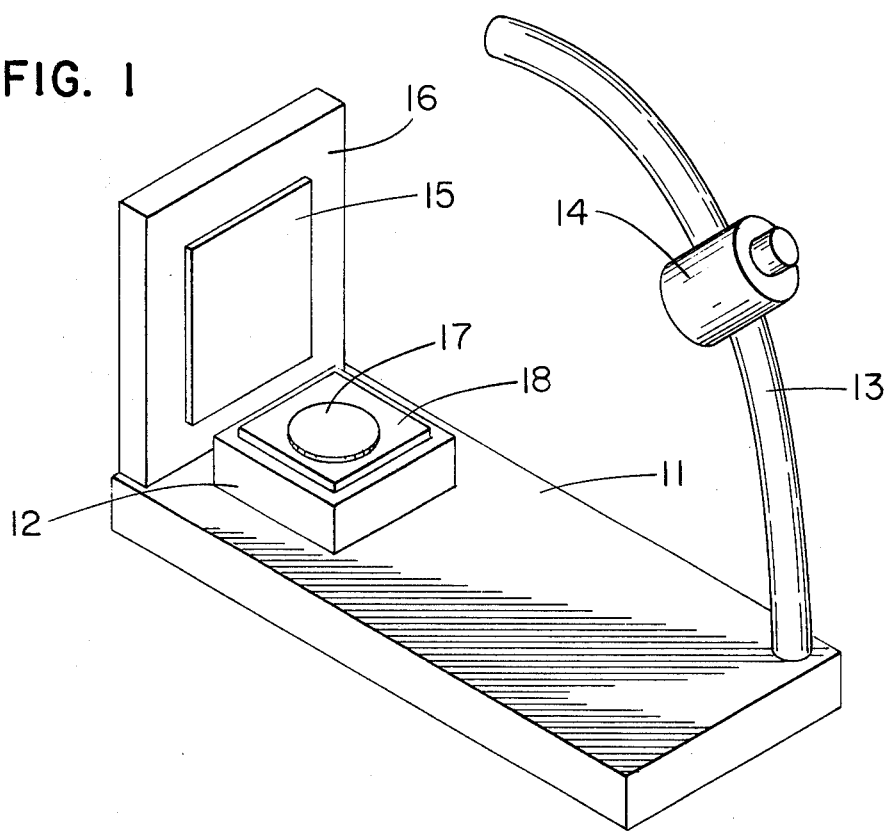
FIG. 1 is a perspective representation of the testing device of this invention.
Figure 2:
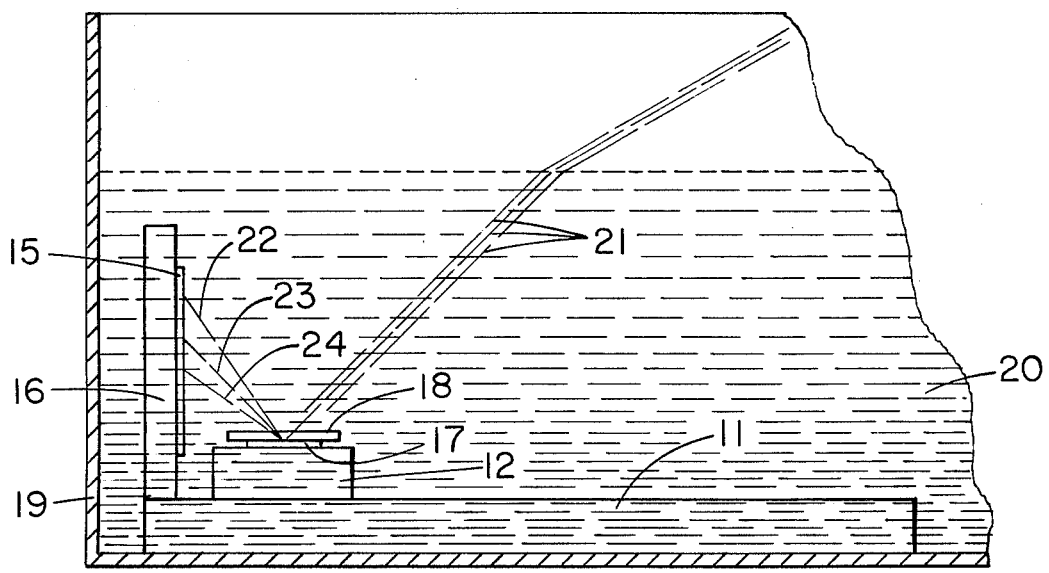
FIG. 2 is a partially-sectioned representation of the testing device of this invention in operation and includes a representation of a path of light incident on a liquid crystal sample in the device.

The fluid 20 is important for two reasons. First, the fluid 20 serves as a constant temperature bath; and second, the fluid 20 alters the critical angle of light transmission and provides a more favorable environment for light refraction and scattering. As a constant temperature bath, the fluid 20 can be heated or cooled in a controlled manner or the temperature can merely be monitored.

DESCRIPTION OF PREFERRED EMBODIMENTS

In operation, a liquid crystal sample, for example a composition of 44.0, weight percent cholesteryl nonanoate, 10.0 weight percent cholesteryl chloride, and 46.0 weight percent isostearyl cholesteryl carbonate is placed on a blackened microscope or equivalent mounting block means and is covered with a protective cover. Liquid crystal materials have an index of refraction of approximately 1.5 and, for that reason, protective covers are preferably of some material having a similar index of refraction, and are most often glass.

The device, with mounted film of liquid crystal, sample is immersed, as previously described, and the light source is adjusted such that incident white light falls on the sample. The angle of light incidence can be from 20° to about 70° from the normal and 35° to 40° is usually used. The fluid temperature is adjusted or observed and the nature of the light projected onto the screen is noted. Generally a test is started with the fluid temperature below the color advent temperature of the liquid crystal material under investigation. At that low temperature, the projection screen intercepts and displays a white image. The fluid temperature is slowly raised and, at the color advent temperature, red reflected light appears on the reflected image. In the case of the example composition disclosed above, the color advent temperature is about 21.0° centigrade. As the fluid temperature is increased further, the reflected red light moves off of the screen projection of reflected light and other spectral hues successively move up and off. Additional temperature increase eventually causes all reflected colors to move up and out of the projected image, in order. The upper limit of temperature response is generally taken to be the temperature at which reflected blue light moves up and out of the projected image. For the example composition that upper temperature limit is about 25.0° centigrade.

Similar tests can be conducted for any and all light scattering cholesteric liquid crystal formulations.

This device and procedure can be used to determine any temperature response or range desired or required by specific conditions. For example, the temperature advent and range for blue reflected color could be determined or the intensity of a particular reflected color can be compared with some standard composition or color. A spectral response for one composition can be compared with some standard response by mounting a color reproduction of the standard response on one-half of the projector screen and adjusting the fluid temperature so that the reflected spectrum is in comparative correspondence with the standard.

The index of refraction of the fluid is important in practice of this invention because the scattered spectrum of light is more readily observed when the light scattering occurs into a medium of relatively high index of refraction. Light is scattered from the liquid crystal material in accordance with the following, well known, equation:

$$L = L_o \left[ \cos \frac{1}{2} \left\{ \sin^{-1}\left(\frac{n_o}{n_l} \sin \theta_i\right) + \sin^{-1}\left(\frac{n_o}{n_l} \sin \theta_s\right) \right\} \right]$$

wherein
L is the wavelength of light observed on the projection screen;
$L_o$ is the wavelength of light which would be reflected at normal incidence and viewing of a given liquid crystal sample at a particular temperature;
$n_o$ is the index of refraction of the ambient medium;
$n_l$ is the index of refraction of the liquid crystal medium (taken herein as 1.5);
$\phi_i$ is the angle of incidence for the incident white light;
$\phi_s$ is the angle of reflection for a scattered component of the incident white light.

As previously stated, the protective cover is selected to have an index of refraction nearly the same as the liquid crystal material and, for purposes of light path analysis, the cover and the liquid crystal material can be taken as a single medium. The critical angle for light to escape from one medium to another is, $$\sin^{-1}\left(\frac{n_o}{n_l}\right) = \theta_c.$$

If the angle of a light path approaching a medium of lower index of refraction is greater than the critical angle, the light will be reflected internally and will not pass from one medium to the other. Fluids for use in this invention must be clear and preferably colorless, relatively inert and non-corrosive. Eligible fluids should have indexes of refraction of from about 1.2 to about 1.5. As a practical matter, water is most often used and will be used herein for exemplary calculations to exhibit the benefits of the invention. Various, low-vapor-pressure, silicone fluids, having an index of refraction of about 1.4 to 1.5, are also eligible for use herein as are also, commercially available fluorocarbon liquids such as, heptacosafluorotributylamine having an index of refraction of about 1.29 and a mixture of perfluors cyclic ether isomers $C_8F_{16}O$ having an index of refraction of about 1.28.

In the table below, comparison calculations are presented for air and water as fluids in which to practice the invention. The calculations utilize a hypothetical liquid crystal sample at a temperature which would exhibit a normal reflected wavelength of 0.650 microns when lighted normal by white light. $L_o = 0.650$ (red). The angle of incidence ($\phi_i$) is taken to be 20°, 45°, and 70° in order to provide a range of operating conditions. The angle of scattered reflected light ($\phi_s$) is taken to be 20° and the critical angle to indicate the range of hues reflected at a particular set of operating conditions.

| Light Scattering Comparison Table ($L_o = 0.650$) | | | | | | |
|---|---|---|---|---|---|---|
| air $n_o = 1.0$ $\theta_c = 41.8°$ | | | | water $n_o = 1.33$ $\theta_c = 62.5°$ | | |
| $\theta_i$ | $\theta_s$ | L | L | $\theta_s$ | L | L |
| 20 | 20 | .632 red-orange | .021 | 20 | .618 orange-red | .084 |
|  | 41.8 | .611 orange-red |  | 62.5 | .534 green-yellow |  |
| 45 | 20 | .607 orange | .032 | 20 | .572 yellow-green | .115 |
|  | 41.8 | .575 yellow |  | 62.5 | .457 blue-violet |  |
| 70 | 20 | .584 yellow | .037 | 20 | .419 green | .137 |
|  | 41.8 | .547 yellow-green |  | 62.5 | .382 ultraviolet |  |

From the table, above, it is clearly seen that the use of an air system results in rather narrow, nearly single-color, scattered hues at any angle of incidence. On the other hand, the use of water as the fluid provides a spectrum of scattered hues 3.5 to 4.0 times as broad as the spectrum projected in air.

What is claimed is:

1. A cholesteric liquid crystal testing device comprising a light absorbing mounting surface for receiving a film comprising cholesteric liquid crystal material, a light source directed to the mounting surface and adjustable to vary the angle of light incident on the mounting surface between about 20° and about 70°, and a light reflecting surface located substantially perpendicular to the mounting surface to intercept light directed from the light source and scattered in a spectral hue from a film comprising cholesteric liquid crystals located on said mounting surface.

2. The testing device of claim 1 wherein the mounting surface is black.

3. The testing device of claim 1 wherein the light reflecting surface is white.

4. The testing device of claim 1 wherein the mounting surface is located on a mounting block.

5. The testing device of claim 1 wherein the mounting surface and the light reflecting surface are immersed in a fluid.

6. The testing device of claim 5 wherein the fluid has an index of refraction of about 1.2 to about 1.5.

7. The testing device of claim 6 wherein the fluid is water.

8. A process for testing the spectral response of a temperature sensitive, light scattering, cholesteric liquid crystal material comprising the steps of: (a) placing a film comprising the cholesteric liquid crystal material on a light absorbing mounting surface; (b) immersing the so-placed film in a fluid having an index of refraction between about 1.2 and 1.5; (c) directing a white light source into the fluid and onto the film at an angle of about 20° to 70° with a normal to the film; (d) intercepting at least a portion of the light reflected and scattered from the film onto a light reflecting surface located perpendicular to the mounting surface and immersed in the fluid.

9. The process of claim 8 wherein there is the additional step of (e) adjusting the temperature of the fluid to cause color advent in the cholesteric liquid crystal film and spectral display of color on the light reflecting surface.

10. The process of claim 9 wherein the fluid is water.

* * * * *